US011203347B2

United States Patent
Matsuura et al.

(10) Patent No.: US 11,203,347 B2
(45) Date of Patent: Dec. 21, 2021

(54) IN-VEHICLE DEVICE, INFORMATION MANAGEMENT SERVER, INFORMATION MANAGEMENT SYSTEM, AND METHOD

(71) Applicant: HONDA MOTOR CO., LTD., Tokyo (JP)

(72) Inventors: Kohei Matsuura, Wako (JP); Yu Oishi, Tokyo (JP); Tomoyuki Takewaka, Tokyo (JP)

(73) Assignee: HONDA MOTOR CO., LTD., Tokyo (JP)

( * ) Notice: Subject to any disclaimer, the term of this patent is extended or adjusted under 35 U.S.C. 154(b) by 274 days.

(21) Appl. No.: 16/576,419

(22) Filed: Sep. 19, 2019

(65) Prior Publication Data

US 2020/0010091 A1   Jan. 9, 2020

Related U.S. Application Data (63) Continuation of application No. PCT/JP2017/013781, filed on Mar. 31, 2017.

(51) Int. Cl.
*G10L 15/22* (2006.01)
*B60W 40/09* (2012.01)
(Continued)

(52) U.S. Cl.
CPC ............ *B60W 40/09* (2013.01); *B60W 50/14* (2013.01); *G06K 9/00845* (2013.01);
(Continued)

(58) Field of Classification Search
CPC ................. B60W 40/09; B60W 50/14; B60W 2040/0872; B60W 2540/22;
(Continued)

(56) References Cited

U.S. PATENT DOCUMENTS 8,140,241 B2   3/2012 Takeda et al.
9,493,118 B1 * 11/2016 Laur .................... B60K 28/066
(Continued)

FOREIGN PATENT DOCUMENTS

CN      106469509 A    3/2017
JP    2007-271959 A   10/2007
(Continued)

OTHER PUBLICATIONS

Examination Report for Indian Patent Application No. 201947039160 dated Feb. 23, 2021.
(Continued)

*Primary Examiner* — Munear T Akki
(74) *Attorney, Agent, or Firm* — Thomas | Horstemeyer, LLP (57) ABSTRACT

The present invention provides an in-vehicle device that provides a driving guidance to a driver, comprising: a selection unit for selecting ideal traveling information from a plurality of pieces of ideal traveling information associated with a plurality of skill levels, respectively, in accordance with an estimation result of a feeling of the driver; a determination unit for determining, for each of a plurality of items to provide a driving guidance, whether a difference between traveling information detected by a sensor of a vehicle during traveling and the ideal traveling information selected by the selection unit falls within an allowable range; and a notification unit for notifying the driver of an item for which the determination unit determines that the difference does not fall within the allowable range in the plurality of items.

17 Claims, 8 Drawing Sheets

(51) Int. Cl.
*B60W 50/14* (2020.01)
*G06K 9/00* (2006.01)
*B60W 40/08* (2012.01)

(52) U.S. Cl.
CPC . *B60W 2040/0872* (2013.01); *B60W 2540/22* (2013.01); *B60W 2540/30* (2013.01)

(58) Field of Classification Search
CPC ....... B60W 2540/30; B60W 2540/223; B60W 40/08; G06K 9/00845; G06K 2009/00939; G06K 9/00302; A61B 5/18; G08G 1/16
See application file for complete search history.

(56) References Cited

U.S. PATENT DOCUMENTS

| | | | |
|---|---|---|---|
| 9,978,279 B2 | 5/2018 | Suzuno | |
| 10,528,044 B2 | 1/2020 | Emura et al. | |
| 2009/0234552 A1 | 9/2009 | Takeda et al. | |
| 2012/0239286 A1* | 9/2012 | Mizuguchi | G08G 1/162 701/301 |
| 2013/0194099 A1* | 8/2013 | Nagata | A61B 5/1079 340/575 |
| 2015/0179073 A1 | 6/2015 | Suzuno | |
| 2015/0254977 A1* | 9/2015 | Grabow | G08G 1/163 340/903 |
| 2016/0042642 A1* | 2/2016 | Yamashiro | G09B 29/10 340/990 |
| 2017/0200449 A1* | 7/2017 | Penilla | G10L 15/063 |
| 2017/0355379 A1* | 12/2017 | Hamaguchi | B60W 40/08 |
| 2018/0113454 A1 | 4/2018 | Emura et al. | |
| 2018/0319279 A1* | 11/2018 | Ikeda | G06K 9/00845 |
| 2019/0114913 A1* | 4/2019 | Hori | G08G 1/164 |

FOREIGN PATENT DOCUMENTS

| | | |
|---|---|---|
| JP | 2007-272834 A | 10/2007 |
| JP | 2007-284049 A | 11/2007 |
| JP | 2008-056059 A | 3/2008 |
| JP | 2008-070965 A | 3/2008 |
| JP | 2009-234508 A | 10/2009 |
| JP | 2010-231776 A | 10/2010 |
| JP | 2012-112853 A | 6/2012 |
| WO | 2014/024606 A1 | 2/2014 |
| WO | 2016/120994 A1 | 8/2016 |
| WO | 2016/199379 A1 | 12/2016 |
| WO | 2018/179406 A1 | 10/2018 |

OTHER PUBLICATIONS

Chinese Office Action for Chines Patent Application No. 201780088629.8 dated Jun. 25, 2021 (partially translated).

Lin Qiwan, Research on Driving Behavior Based on Emotional Computing, Chinese Master's Theses Full-text Database Engineering Science and Technology II, Sep. 16, 2014 thru Oct. 15, 2014, section 2.3 on pp. 15-16, issue 10, China Academic Journals, Beijing, China.

International Search Report for PCT/JP2017/013781 dated Jul. 4, 2017 (partially translated).

IPRP for PCT/JP2017/013781 mailed Dec. 4, 2018.

* cited by examiner

| TRAVELING ROUTE | SKILL LEVEL | MODEL DRIVER | DATA OF IDEAL TRAVELING STATE | | |
|---|---|---|---|---|---|
| | | | OPERATION DATA | DRIVE POSTURE DATA | VEHICLE POSTURE DATA |
| ○○PATH_ | A | Mr. H | ○○PATH_ OPERATION DATA A | ○○PATH_ DRIVE POSTURE DATA A | ○○PATH_ VEHICLE POSTURE DATA A |
| | B | Mr. H | ○○PATH_ OPERATION DATA B | ○○PATH_ DRIVE POSTURE DATA B | ○○PATH_ VEHICLE POSTURE DATA B |
| | C | Mr. Y | ○○PATH_ OPERATION DATA C | ○○PATH_ DRIVE POSTURE DATA C | ○○PATH_ VEHICLE POSTURE DATA C |
| | D | Mr. Y | ○○PATH_ OPERATION DATA D | ○○PATH_ DRIVE POSTURE DATA D | ○○PATH_ VEHICLE POSTURE DATA D |
| △△PASS_ | A | Mr. S | △△PASS_ OPERATION DATA A | △△PASS_ DRIVE POSTURE DATA A | △△PASS_ VEHICLE POSTURE DATA A |
| | B | Mr. H | △△PASS_ OPERATION DATA B | △△PASS_ DRIVE POSTURE DATA B | △△PASS_ VEHICLE POSTURE DATA B |
| | C | Mr. Y | △△PASS_ OPERATION DATA C | △△PASS_ DRIVE POSTURE DATA C | △△PASS_ VEHICLE POSTURE DATA C |
| | D | Mr. Y | △△PASS_ OPERATION DATA D | △△PASS_ DRIVE POSTURE DATA D | △△PASS_ VEHICLE POSTURE DATA D |
| ... | | | | | |

| TRAVELING ROUTE | ITEM | SENSOR |
|---|---|---|
| OPERATION OF VEHICLE | SPEED | SPEED SENSOR |
| | ACCELERATION | ACCELERATION SENSOR |
| | THROTTLE OPENING | THROTTLE OPENING SENSOR |
| | BRAKE AMOUNT | BRAKE AMOUNT SENSOR |
| | SHIFT POSITION | SHIFT POSITION SENSOR |
| DRIVER POSTURE | HEAD, SHOULDER | IN-VEHICLE SENSOR (CENTER SENSOR) |
| | ELBOW, KNEE | IN-VEHICLE SENSOR (RIGHT SENSOR, LEFT SENSOR) |
| | WAIST | IN-VEHICLE SENSOR (CENTER SENSOR), LOAD SENSOR |
| VEHICLE POSTURE | BANK ANGLE | INCLINATION SENSOR |
| | STEERING ANGLE | STEERING ANGLE SENSOR |
| ⋮ | | |

IN-VEHICLE DEVICE, INFORMATION MANAGEMENT SERVER, INFORMATION MANAGEMENT SYSTEM, AND METHOD

CROSS-REFERENCE TO RELATED APPLICATION

This application is a continuation of International Patent Application No. PCT/JP2017/013781 filed on Mar. 31, 2017, the entire disclosures of which are incorporated herein by reference.

BACKGROUND OF THE INVENTION

Field of the Invention

The present invention relates to an in-vehicle device, an information management server, an information management system, and a method.

Background Art

There has been proposed estimating a possibility that the feeling (psychological state) of a driver may change in a case in which a current situation is similar to a situation at the time of an accident and controlling a vehicle or making a notification to the driver based on the estimated feeling (PTL 1).

In a system configured to provide a driving guidance to a driver, it is desired to notify the driver of guidance information to efficiently improve a driving skill. PTL 1 discloses making a notification to promote relaxation or safe driving to a driver, but is not associated with a driving guidance to the driver.

It is an object of the present invention to provide a driving guidance to efficiently improve a driving skill.

CITATION LIST

Patent Literature

PTL 1: Japanese Patent Laid-Open No. 2008-070965

SUMMARY OF THE INVENTION

According to the present invention, there is provided an in-vehicle device that provides a driving guidance to a driver, comprising: a selection unit for selecting ideal traveling information from a plurality of pieces of ideal traveling information associated with a plurality of skill levels, respectively, in accordance with an estimation result of a feeling of the driver; a determination unit for determining, for each of a plurality of items to provide a driving guidance, whether a difference between traveling information detected by a sensor of a vehicle during traveling and the ideal traveling information selected by the selection unit falls within an allowable range; and a notification unit for notifying the driver of an item for which the determination unit determines that the difference does not fall within the allowable range in the plurality of items.

Further features of the present invention will become apparent from the following description of exemplary embodiments with reference to the attached drawings.

DESCRIPTION OF THE EMBODIMENTS

A system 100 according to an embodiment of the present invention will be described. The system 100 according to this embodiment is a system that provides a driving guidance to a driver. In this embodiment, an example in which a driving guidance is provided to the driver of a straddle type vehicle (for example, a two-wheeled vehicle) will be described. However, this system can similarly be applied to a case in which a driving guidance is provided to the driver of another vehicle (four-wheeled vehicle or the like).

<System Arrangement>

Figure 1:
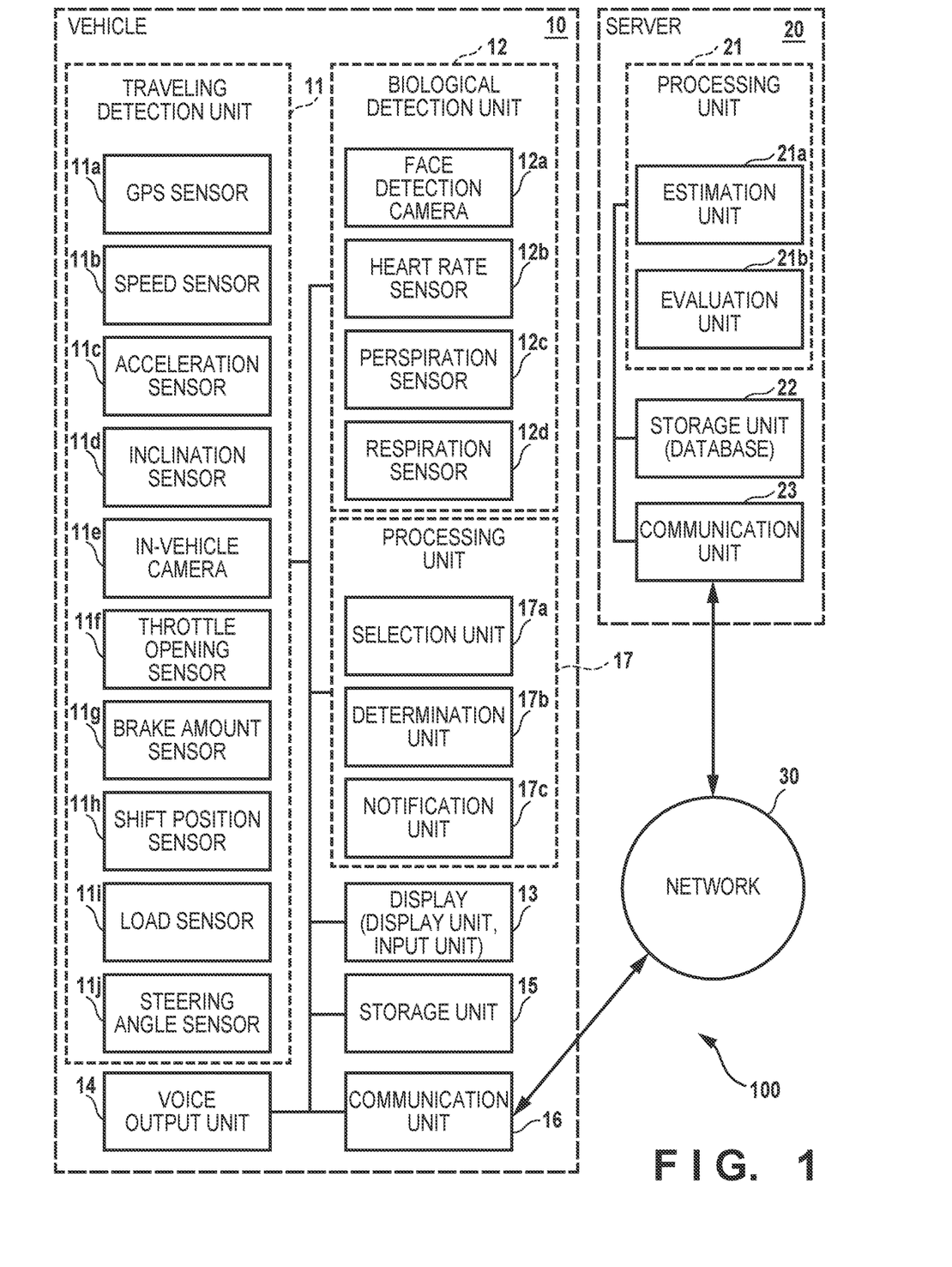
FIG. 1 is a block diagram showing the arrangement of a system.

FIG. 1 is a block diagram showing the arrangement of the system 100 according to this embodiment. The system 100 according to this embodiment includes a vehicle 10 (two-wheeled vehicle) and a server 20.

The vehicle 10 includes, as an in-vehicle device, a traveling detection unit 11 that detects the traveling state of the vehicle 10, a biological detection unit 12 that detects the biological state of the driver of the vehicle 10, a display 13, a voice output unit 14, a storage unit 15 (memory), a communication unit 16 that communicates with the server 20 via a network 30, and a processing unit 17 (CPU). The display 13 uses, for example, a touch panel type LCD (Liquid Crystal Display) and can function as both a display unit and an input unit. However, the present invention is not limited to this, and an input unit may be provided independently of the display unit serving as a display unit. The voice output unit 14 outputs a voice signal to, for example, an earphone worn by the driver wirelessly or via a cable.

The traveling detection unit 11 includes, for example, a GPS sensor 11a (a global positioning system sensor, also called a position sensor) that detects the position of the vehicle 10, a speed sensor 11b that detects the speed of the vehicle 10, an acceleration sensor 11c that detects the acceleration of the vehicle 10, an inclination sensor 11d that detects the inclination (bank angle) of the vehicle 10, and an in-vehicle camera 11e that captures the driver who is riding the vehicle 10. The in-vehicle camera 11e includes, for example, a center camera that captures the head, the body, and the like of the driver, a right camera that captures the right elbow, the right knee, and the like of the driver, and a left camera that captures the left elbow, the left knee, and the like of the driver. Each camera can include a wide-angle lens. The traveling detection unit 11 can also include a throttle opening sensor 11f that detects the opening of the throttle, a brake amount sensor 11g that detects a brake amount, a shift position sensor 11h that detects a shift position, a load sensor 11i that detects the load of the driver on a seat, and a steering angle sensor 11j that detects the steering angle.

The biological detection unit 12 includes a face detection camera 12a that detects (capture) the face of the driver, and sensors (a heart rate sensor 12b, a perspiration sensor 12c, and a respiration sensor 12d) that detect the heart rate, perspiration, respiration, and the like of the driver. The face detection camera 12a can be provided, for example, in a helmet worn by the driver. However, the present invention is not limited to this, and the face detection camera 12a may be provided on the vehicle 10. In addition, the processing unit 17 includes a selection unit 17a (selection means) that selects information representing an ideal traveling state in accordance with the feeling of the driver, a determination unit 17b (determination means) that determines whether the difference between the ideal traveling state and the traveling state detected by the traveling detection unit during traveling falls within an allowable range, and a notification unit 17c (notification means) that notifies the driver of the determination result of the determination unit.

The server 20 includes a processing unit 21 (CPU), a storage unit 22 (database), and a communication unit 23 that communicates with the vehicle 10 via the network 30. The processing unit 21 includes an estimation unit 21a that estimates the feeling of the driver based on the detection results of the traveling detection unit 11 and the biological detection unit 12 of the vehicle 10, and an evaluation unit 21b that evaluates the skill level of the driver based on the detection result of the traveling detection unit 11.

<Processing of Vehicle 10>

Figure 2:
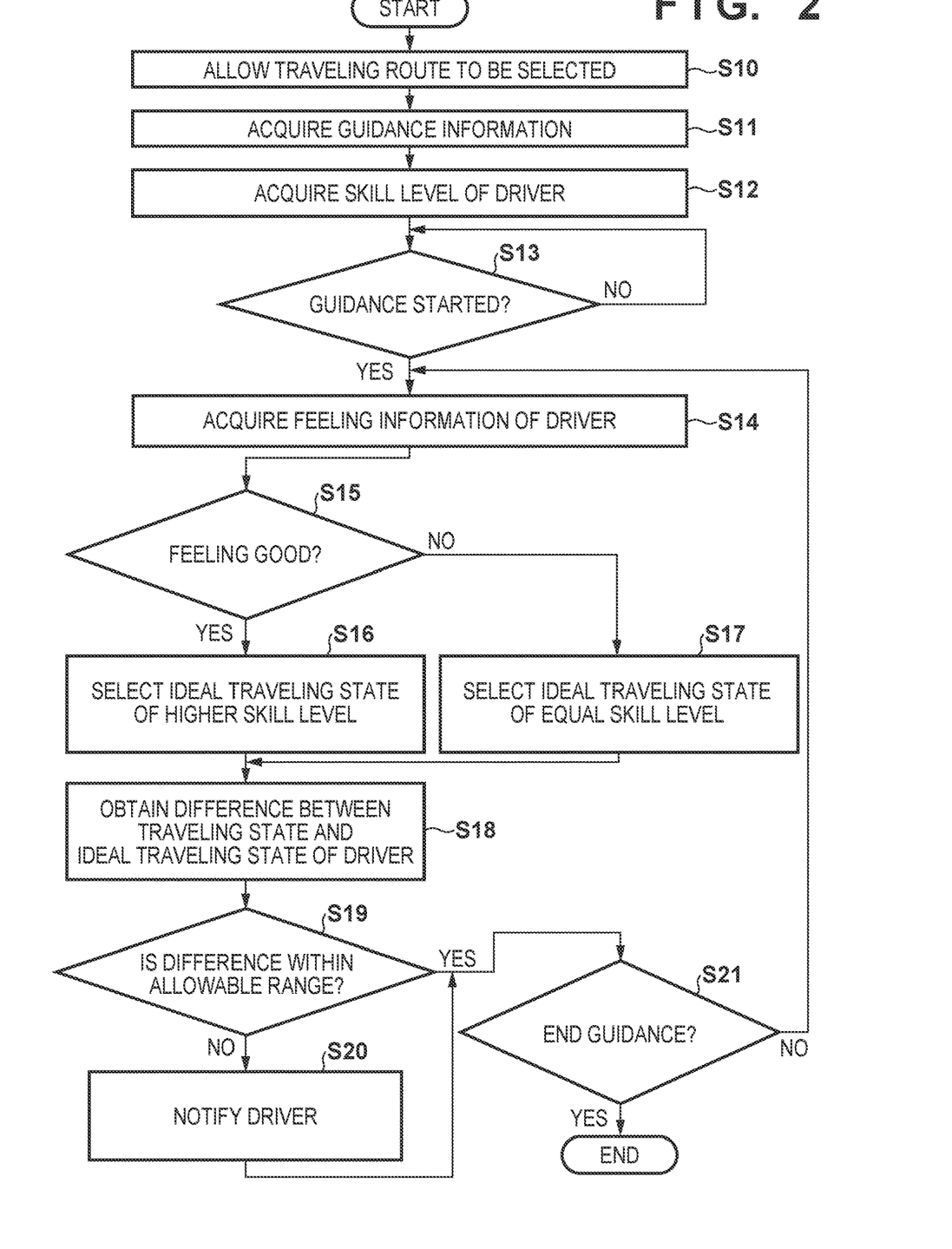
FIG. 2 is a flowchart showing the operation procedure of a vehicle.

FIG. 2 is a flowchart showing the operation procedure of the vehicle 10 according to this embodiment. The steps of the flowchart shown in FIG. 2 are performed by the processing unit 17 of the vehicle 10. Additionally, in the vehicle 10, the traveling state and the biological state of the driver are always detected by the traveling detection unit 11 and the biological detection unit 12.

In step S10, the processing unit 17 acquires a plurality of pieces of traveling route information each including guidance information from the server 20 via the communication unit 16, and displays the acquired plurality of pieces of traveling route information on the display 13. The plurality of pieces of traveling route information may be displayed, for example, in a superimposed manner on a map displayed on the display 13, or may be displayed on the display 13 in the order of place names of the traveling routes. This allows the driver to select a traveling route to travel via the display 13. In addition, the processing unit 17 may automatically acquire the traveling route that the driver should travel based on position information detected by the GPS sensor 11a.

Figure 3:
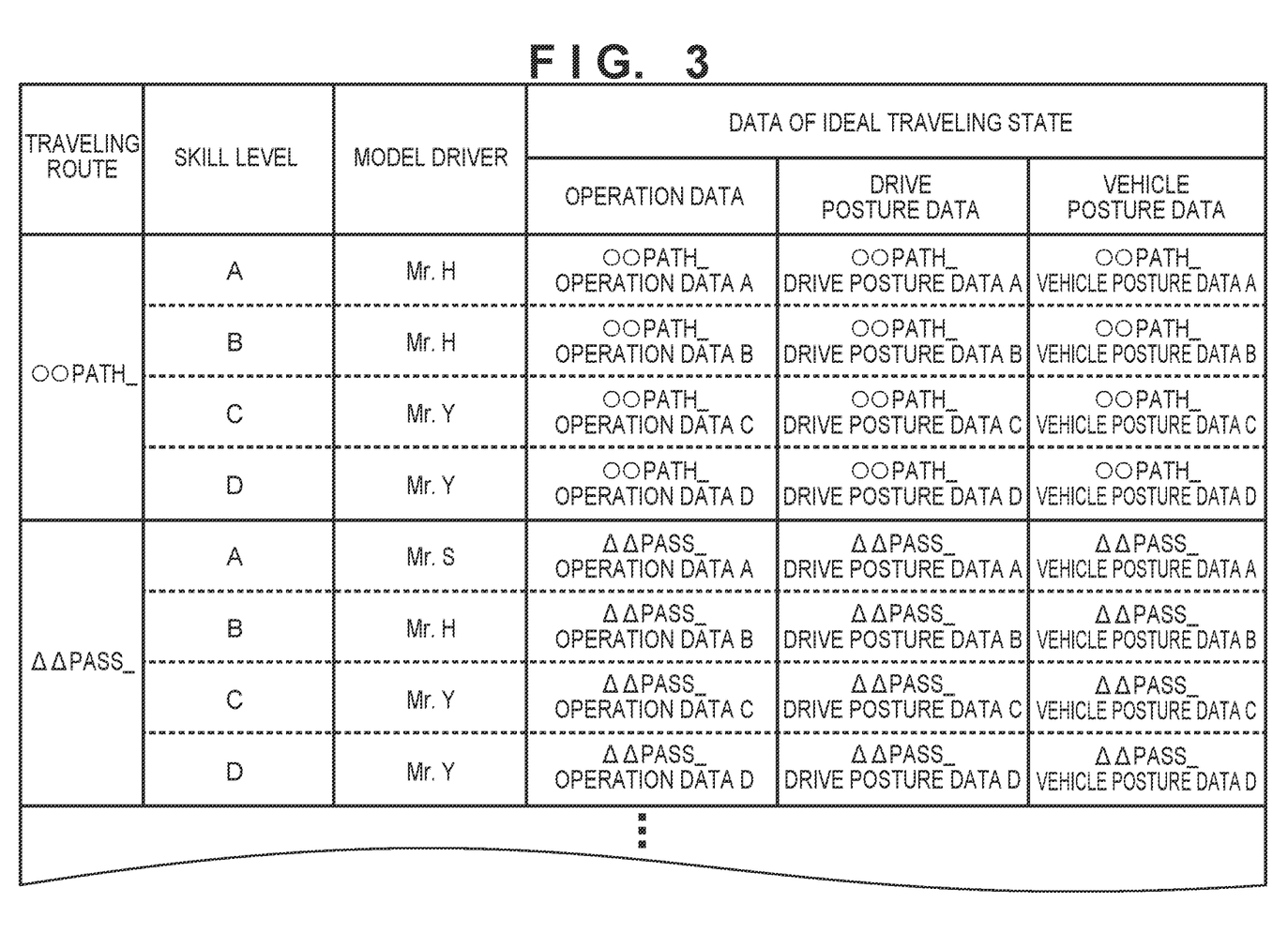
FIG. 3 is a view showing guidance information stored in a server.

In step S11, the processing unit 17 acquires guidance information concerning the traveling route selected by the driver from the server 20 via the communication unit 16. FIG. 3 is a view showing guidance information stored in the server 20 (storage unit 22). As shown in FIG. 3, guidance information is stored in the server 20 on a traveling route basis, and includes information (ideal traveling information) representing an ideal traveling state for a position on a traveling route for each of a plurality of skill levels. The information representing the ideal traveling state can include, for example, data (operation data) of an ideal traveling state concerning the operation of the vehicle 10 such as a speed, a throttle opening, a brake amount, and a shift position, data (driver posture data) of an ideal traveling state concerning the posture of the driver such as a head, shoulders, elbows, and knees, and data (vehicle posture data) of an ideal traveling state concerning the posture of the vehicle 10 such as a bank angle and a steering angle.

Figure 4:
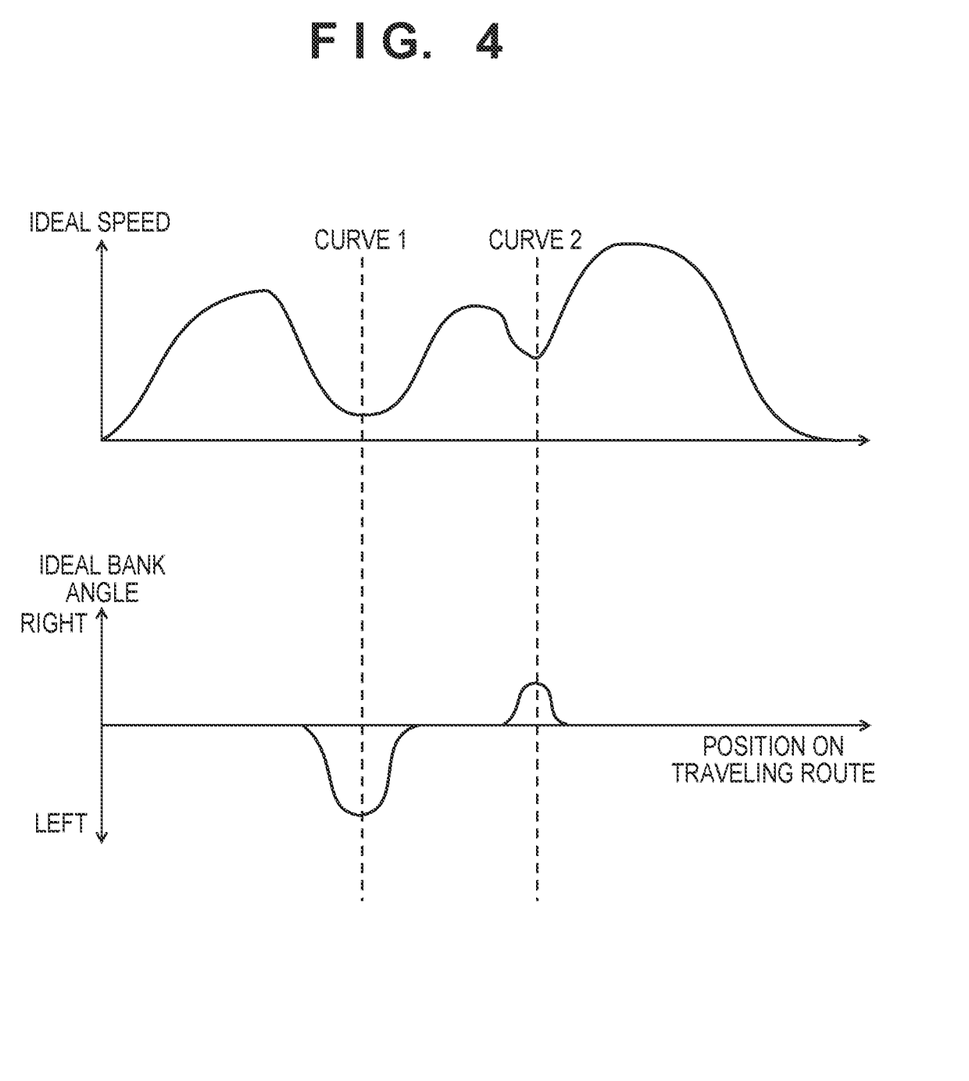
FIG. 4 shows charts illustrating an ideal speed and an ideal bank angle for a position on a traveling route.

FIG. 4 shows charts illustrating an ideal speed and an ideal bank angle for a position on a traveling route as an example of information representing an ideal traveling state for a position on a traveling route concerning one skill level. The abscissa represents a position on a traveling route, and the ordinate represents an ideal speed or an ideal bank angle. Such information representing the ideal traveling state is preferably generated based on data obtained by, for example, making a model driver such as a professional driver (a professional rider or a professional driver) travel the traveling route in advance, as shown in FIG. 3. However, the information may be generated based on the average value or the like of data obtained when a plurality of general drivers travel the traveling route.

In step S12, the processing unit 17 acquires the skill level of the driver from the server 20 via the communication unit 16. The skill level of the driver is determined based on the difference between the ideal traveling state and the traveling state of the driver obtained in the driving guidance so far, and stored in the server 20 (storage unit 22) for each driver.

In step S13, the processing unit 17 judges whether to start a driving guidance to the driver. The judgment concerning whether to start a driving guidance can be performed by judging, based on, for example, the detection result of the position of the vehicle 10 by the GPS sensor 11a or the detection results of the speed sensor 11b and the acceleration sensor 11c, whether the driver has started traveling on the traveling route. Alternatively, the judgment may be done when the driver inputs, via the input unit, an instruction signal used to start the driving guidance by, for example, pressing a "guidance start" button displayed on the touch panel type display 13. Upon judging to start the driving guidance, transmission of the detection result (traveling information) of the traveling detection unit 11 and the detection result (biological information) of the biological detection unit 12 to the server 20 is started, and the process advances to step S14.

In step S14, the processing unit 17 acquires information (feeling information) representing whether the feeling of the driver is good or not from the server 20 via the communication unit 16. "The feeling of the driver is good" indicates, for example, a state in which the driver can concentrate on driving such as a state in which the driver is relax. On the other hand, "the feeling of the driver is not good (bad)" indicates, for example, a state in which the driver cannot concentrate on driving such as a state in which the driver is excessively tense or has concern about driving (afraid of driving). The method of estimating the feeling of the driver by the server 20 will be described later.

Here, improvement of the driving skill by the driving guidance to the driver is often influenced by the feeling of the driver. For example, in a case in which the feeling of the driver is good such as a case in which the driver is relax, the driving skill tends to improve. On the other hand, in a case in which the feeling of the driver is bad such as a case in which the driver is afraid of driving, the driving skill tends to be difficult to improve. That is, in the driving guidance to the driver as well, the feeling of the driver is preferably taken into consideration. Hence, in this embodiment, a driving guidance according to the feeling of the driver is provided.

In step S15, the processing unit 17 determines, based on the feeling information of the driver acquired in step S14, whether the feeling of the driver is good. Upon determining in step S15 that the feeling of the driver is good, the process advances to step S16, and the processing unit 17 (selection unit 17a) selects, of a plurality of ideal traveling states (ideal traveling information) associated with a plurality of skill levels, an ideal traveling state for a skill level higher than the current skill level of the driver. Since the driving skill tends to improve if the feeling of the driver is good, the driving guidance is preferably provided while referring to the skill level higher than the current skill level.

On the other hand, upon judging that the feeling of the driver is bad, the process advances to step S17, and the processing unit 17 (selection unit 17a) selects, of the plurality of ideal traveling states, an ideal traveling state for a skill level equal to the current skill level of the driver. If the feeling of the driver is bad, the driving skill tends to be difficult to improve. In addition, if the driving guidance is provided based on a skill level higher than the current skill level of the driver, the uneasiness of the driver is often aroused, and an accident may occur. For this reason, if the feeling of the driver is uneasiness, the driving guidance is preferably provided while referring to the skill level equal to the current skill level until the driver can drive in a good feeling.

In step S18, for the current position on the traveling route detected by the GPS sensor 11a, the processing unit 17 obtains the difference between the traveling state (traveling information) of the driver detected by the traveling detection unit 11 and the ideal traveling state (ideal traveling information) selected in step S16 or S17. A plurality of items as the traveling states whose differences from ideal traveling states should be obtained include items concerning the operation of the vehicle 10 such as a speed, an acceleration, a throttle opening, a brake amount, and a shift position, items concerning the posture of the driver such as a head, shoulders, elbows, knees, and a waist, and items concerning the posture of the vehicle 10 such as a bank angle and a steering angle, and these are detected by the sensors in the traveling detection unit 11, respectively.

Figure 5:
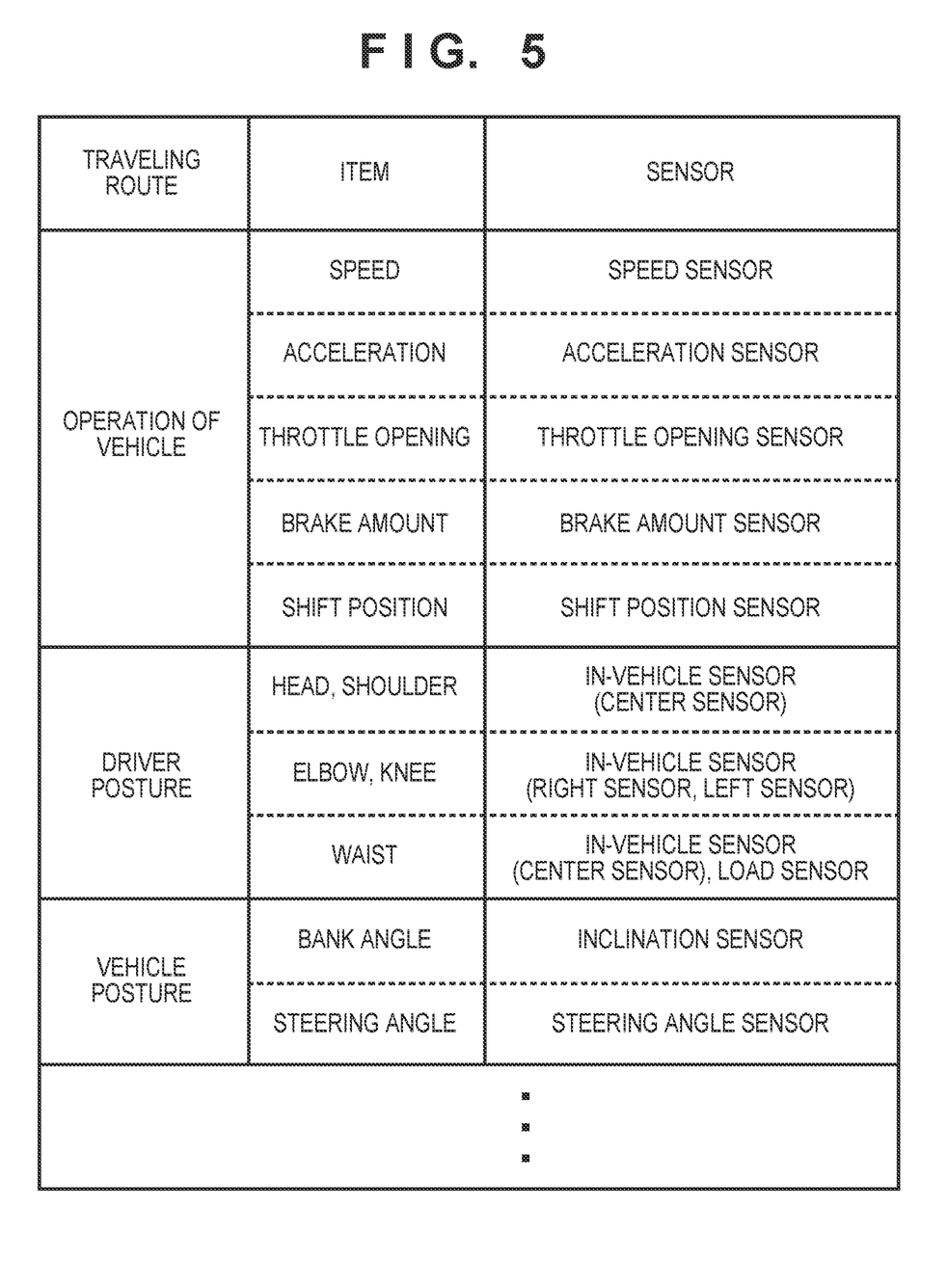
FIG. 5 is a view showing a plurality of items as traveling states and sensors used to detect the traveling states of the items.

FIG. 5 is a view showing a plurality of items as traveling states and sensors used to detect the traveling states of the items. For example, concerning the operation of the vehicle 10, the processing unit 17 obtains the difference between a speed detected by the speed sensor 11b and an ideal value (ideal speed), the difference between an acceleration detected by the acceleration sensor 11c and an ideal value, the difference between a throttle opening detected by the throttle opening sensor 11f and an ideal value, the difference between a brake amount detected by the brake amount sensor 11g and an ideal value, and the difference between a shift position detected by the shift position sensor 11h and an ideal value. Additionally, concerning the posture of the driver, the processing unit 17 obtains the differences between the positions of the head, shoulders, elbows, knees, and waist of the driver (for example, positions with respect to the vehicle 10 (reference position)), which are obtained from the result of processing an image captured by the in-vehicle camera 11e and the detection result of the load sensor 11i provided on the seat, and ideal positions. Concerning the posture of the vehicle 10, the processing unit 17 obtains the difference between the inclination (bank angle) of the vehicle 10 detected by the inclination sensor 11d and an ideal value (ideal bank angle), and the difference between a steering angle detected by the steering angle sensor 11j and an ideal value.

In step S19, the processing unit 17 (determination unit 17b) determines whether the difference for each item obtained in step S18 falls within an allowable range. The allowable range of each item can be set arbitrarily in advance such that, for example, the allowable range concerning the speed is set to ±5 km/h or less, and the allowable range concerning the bank angle is set to ±5° or less. If an item for which the difference obtained in step S18 does not fall within the allowable range is present among the plurality of items, the process advances to step S20. If the differences obtained in step S18 fall within the allowable ranges in all of the plurality of items, the process advances to step S21.

In step S20, the processing unit 17 (notification unit 17c) notifies the driver of the item for which the difference obtained in step S18 does not fall within the allowable range. The notification method will be described later. In step S21, the processing unit 17 judges whether to end the driving guidance to the driver. The judgment concerning whether to end the driving guidance can be performed by judging, based on, for example, the detection result of the position of the vehicle 10 by the GPS sensor 11a or the detection results of the speed sensor 11b and the acceleration sensor 11c, whether the driver has ended traveling on the traveling route. Alternatively, the judgment may be done when the driver inputs, via the input unit, an instruction signal used to end the driving guidance by, for example, pressing a "guidance end" button displayed on the touch panel type display 13. Upon judging to end the driving guidance, the driving guidance is ended, and transmission of the traveling information and the biological information to the server is also ended. On the other hand, if the traveling on the traveling route is not ended, and it is judged not to end the driving guidance, the process returns to step S14.

Figure 6:
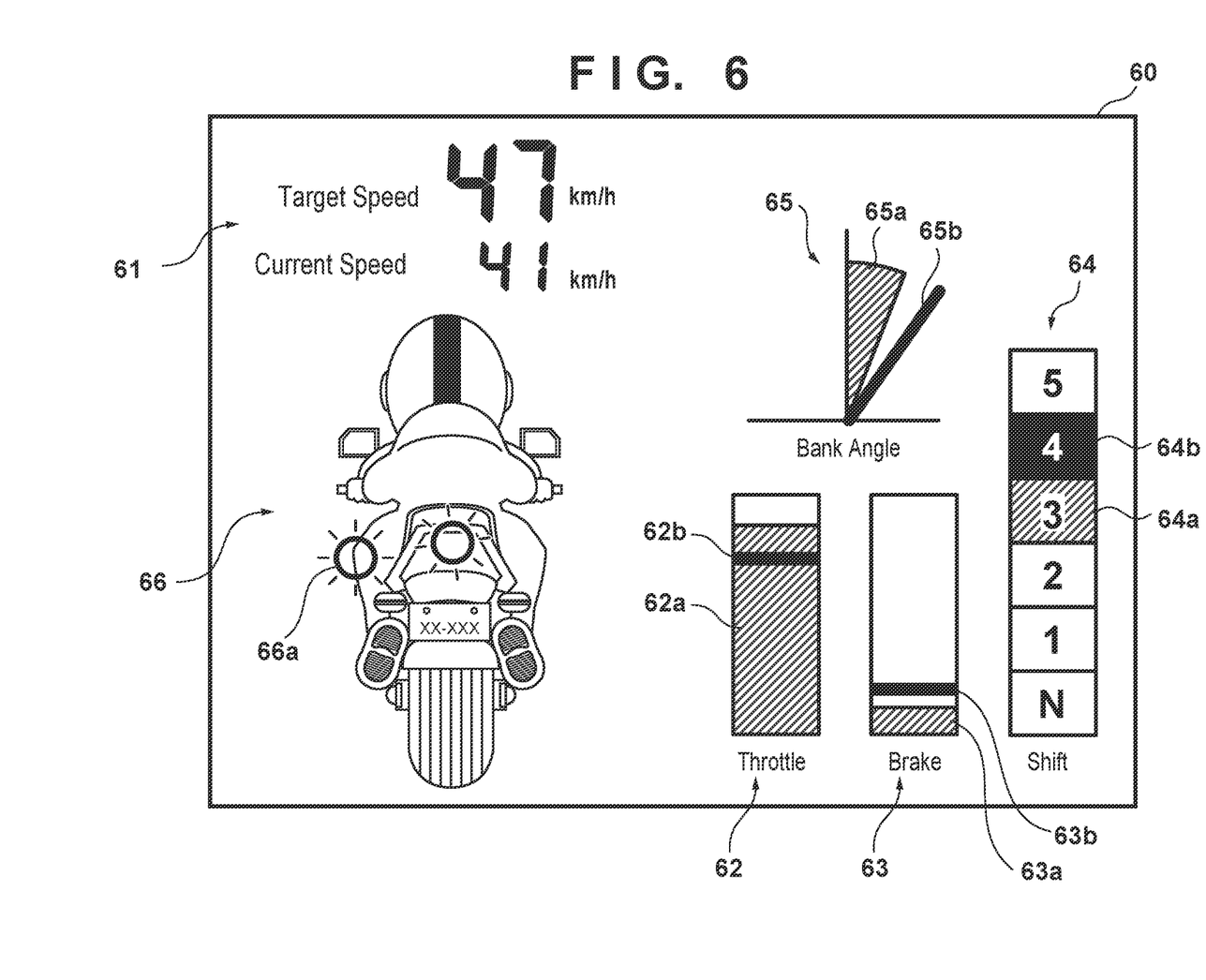
FIG. 6 is a view showing an example of a screen displayed on a display during a driving guidance.

A notification method of notifying the driver of an item for which the difference between the traveling state of the driver and the ideal traveling state does not fall within the allowable range will be described next. FIG. 6 is a view showing an example of a screen 60 displayed on the display 13 during a driving guidance. A speed 61 (a target speed and a current speed), a throttle opening 62, a brake amount 63, a shift position 64, a bank angle 65, and a model 66 of the driver are displayed on the screen 60 shown in FIG. 6.

As for the throttle opening 62, the detection result of the throttle opening sensor 11f is represented by a bar graph 62a, and the ideal value is represented by a thick line 62b. If the difference between the detection result and the ideal value does not fall within the allowable range, highlighting is performed by, for example, blinking the bar graph 62a, thereby making a notification to the driver. As for the brake amount 63, the detection result of the brake amount sensor 11g is represented by a bar graph 63a, and the ideal value is represented by a thick line 63b. If the difference between the detection result and the ideal value does not fall within the allowable range, highlighting is performed by, for example, blinking the bar graph 63b, thereby making a notification to the driver. As for the bank angle 65 as well, the detection result of the inclination sensor 11d is represented by a sector graph 65a, and the ideal value is represented by a thick line 65b. If the difference between the detection result and the ideal value does not fall within the allowable range, highlighting is performed by, for example, blinking the graph 65a, thereby making a notification to the driver. Here, in the example shown in FIG. 6, blinking is performed as highlighting of the item for which the difference from the ideal value is determined not to fall within the allowable range. However, the present invention is not limited to this, and the item need only be displayed to be, for example, distinguishable from other items such that the driver can identify it.

As for the shift position 64, a shift position 64a detected by the shift position sensor 11h and an ideal position 64b are represented by colors or patterns different from each other. If the difference between the shift position 64a and the ideal position 64b does not fall within the allowable range, the shift position 64a is blinked, thereby making a notification to the driver. In addition, as for the positions of the head, shoulders, elbows, knees, and waist of the driver, if the difference from the ideal position does not fall within the allowable range, highlighting is performed by, for example, blinking a circle 66a at a corresponding position on the model 66, thereby making a notification to the driver. In the example shown in FIG. 6, a model of the driver during traveling viewed from the rear side is used. However, the present invention is not limited to this, and, for example, a model of the driver viewed from the front, lateral, or upper side may be used. In this case, the driver may be allowed to select a model to be displayed on the screen 60 from a plurality of models viewed from, for example, the rear, front, lateral, and upper sides. Additionally, in the example shown in FIG. 6, a two-dimensional model of the driver is used. However, the present invention is not limited to this, and a three-dimensional model of the driver, an image obtained by the in-vehicle camera 11e, or the like may be used.

Here, the processing unit 17 may cause the storage unit 15 to successively store the contents displayed on the display 13 during traveling. In this case, the processing unit 17 causes the storage unit 15 to store the contents displayed on the display 13 in correspondence with (in linkage with) the position on the traveling route. Accordingly, after the traveling on the traveling route is ended, and the vehicle is stopped, the driver can confirm the contents displayed on the display 13 during the driving guidance. Additionally, in this embodiment, as for an item outside the allowable range in the plurality of items as the traveling states, the corresponding portion on the display is blinked, thereby making a visual notification to the driver. However, the present invention is not limited to this, and characters may be displayed on the display to notify the driver of the corresponding portion. Alternatively, an audial notification may be made to the driver by a voice or the like. For example, if the throttle opening is less than the allowable range, the processing unit 17 (notification unit 17c) may output, via the voice output unit 14, a voice to promote further opening of the throttle to an earphone or the like worn by the driver.

<Processing of Server 20>

Figure 7:
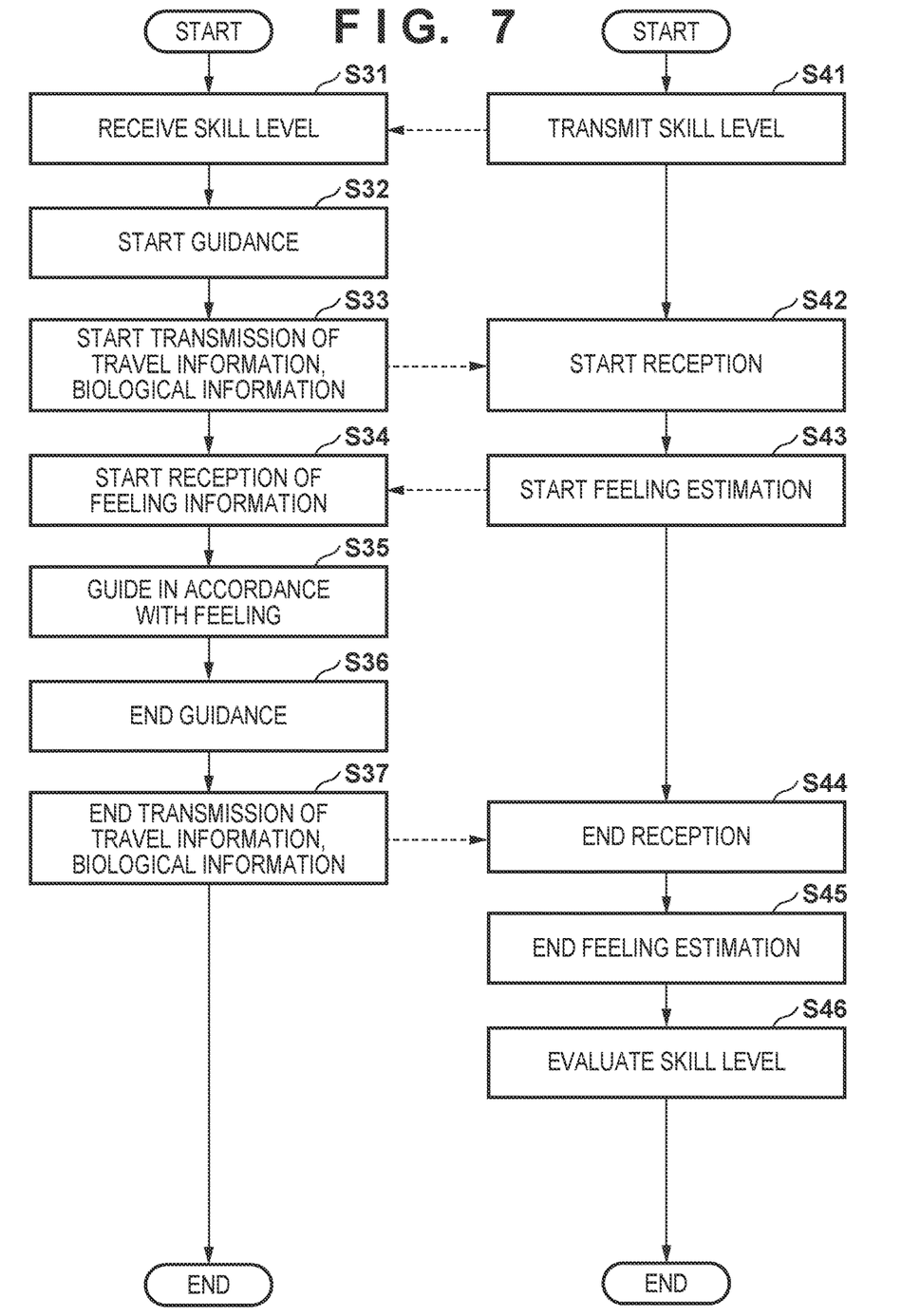
FIG. 7 is a flowchart showing processing of the vehicle and the server.

FIG. 7 is a flowchart showing processing of the vehicle 10 and the server 20. Steps S31 to S37 are processes performed by the vehicle 10, and steps S41 to S46 are processes performed by the server 20.

Processing performed by the vehicle 10 will be described first. Step S31 corresponds to step S12 in FIG. 2 and is processing of receiving the skill level of the driver from the server 20. Steps S32 and S33 correspond to step S13 in FIG. 2, and are processing of starting a driving guidance to the driver and processing of starting transmitting traveling information and biological information to the server 20, respectively. Step S34 corresponds to step S14 in FIG. 2, and is processing of starting receiving (acquiring) the feeling information of the driver. Step S35 corresponds to steps S15 to S20 in FIG. 2, and is processing of providing a driving guidance according to the feeling of the driver to the driver. Steps S36 and S37 correspond to step S21 in FIG. 2, and are processing of ending the driving guidance to the driver and processing of ending transmitting traveling information and biological information to the server 20, respectively.

Processing performed by the server 20 will be described next. In step S41, the server 20 transmits skill level information stored in the storage unit 22 in association with the driver to the vehicle 10 by the communication unit 23. In step S42, the server 20 receives traveling information and biological information from the vehicle 10 by the communication unit 23. In step S43, the server 20 starts estimating the feeling of the driver based on the traveling information and the biological information received (acquired) in step S42. The method of estimating the feeling of the driver will be described later. In step S44, the server 20 ends receiving the traveling information and the biological information. In step S45, the estimation of the feeling of the driver is ended.

In step S46, the skill level of the driver is evaluated based on the traveling information received during the period of steps S42 to S44 (evaluation unit 21b). The evaluation of the skill level can be performed based on the difference between the traveling state of the driver and the ideal traveling state during the period. For example, if the difference between the traveling state and the ideal traveling state falls within the allowable range in all of the plurality of items such as the operation of the vehicle 10, the posture of the driver, and the posture of the vehicle 10, the server 20 raises the skill level of the driver to the skill level referred to as the ideal traveling state and sets it. On the other hand, if at least one item for which the difference between the traveling state and the ideal traveling state does not fall within the allowable range is present among the plurality of items, the server 20 sets the skill level of the driver without changing it. Additionally, if the difference between the traveling state and the ideal traveling state is too large, the skill level of the driver may be lowered and set. The thus set skill level of the driver is stored in the storage unit 22 in association with a driver ID or the like.

<Method of Estimating Feeling of Driver>

The method of estimating the feeling of the driver by the server 20 (estimation unit 21a) will be described next. Based on the result of learning (deep-learning) big data representing the corresponding relationship between feelings (psychological states) and biological states (face images, heart rates, perspiration amounts, and respiration states) acquired for a number of drivers in the past, the server 20 can estimate the feeling of the driver to which the driving guidance is provided.

For example, in a case in which the face image of the driver captured by the face detection camera 12a has a feature such as an unstable line of sight or wrinkles between the eyebrows, the server 20 can judge that the possibility that the driver is feeling uneasy is high. Also in a case in which the heart rate, the perspiration amount, and the respiration state (to be referred to as "the heart rate and the like" hereinafter) detected by the heart rate sensor 12b, the perspiration sensor 12c, and the respiration sensor 12d, respectively, do not fall within normal ranges, the server 20 can judge that the possibility that the driver is feeling uneasy is high. The normal ranges of the heart rate and the like can be set by, for example, referring to the heart rate and the like detected when no driving guidance is provided. Hence, the server 20 preferably acquires the detection results of the heart rate sensor 12b and the like during a period (normal state) without a driving guidance from the vehicle 10, and causes the storage unit 22 to store the detection results as the normal ranges of the heart rate and the like.

Here, even if the heart rate and the like do not fall within the normal ranges, there is a possibility that the driver is not feeling uneasy and is only excited due to the driving guidance. For this reason, the server 20 preferably estimates the feeling of the driver based on the traveling state during the driving guidance as well. For example, a driver who feels uneasy performs awkward driving by non-smoothly changing the throttle opening or the bank angle at a high possibility. However, a driver who feels excited performs smooth driving at a high possibility.

Figure 8:
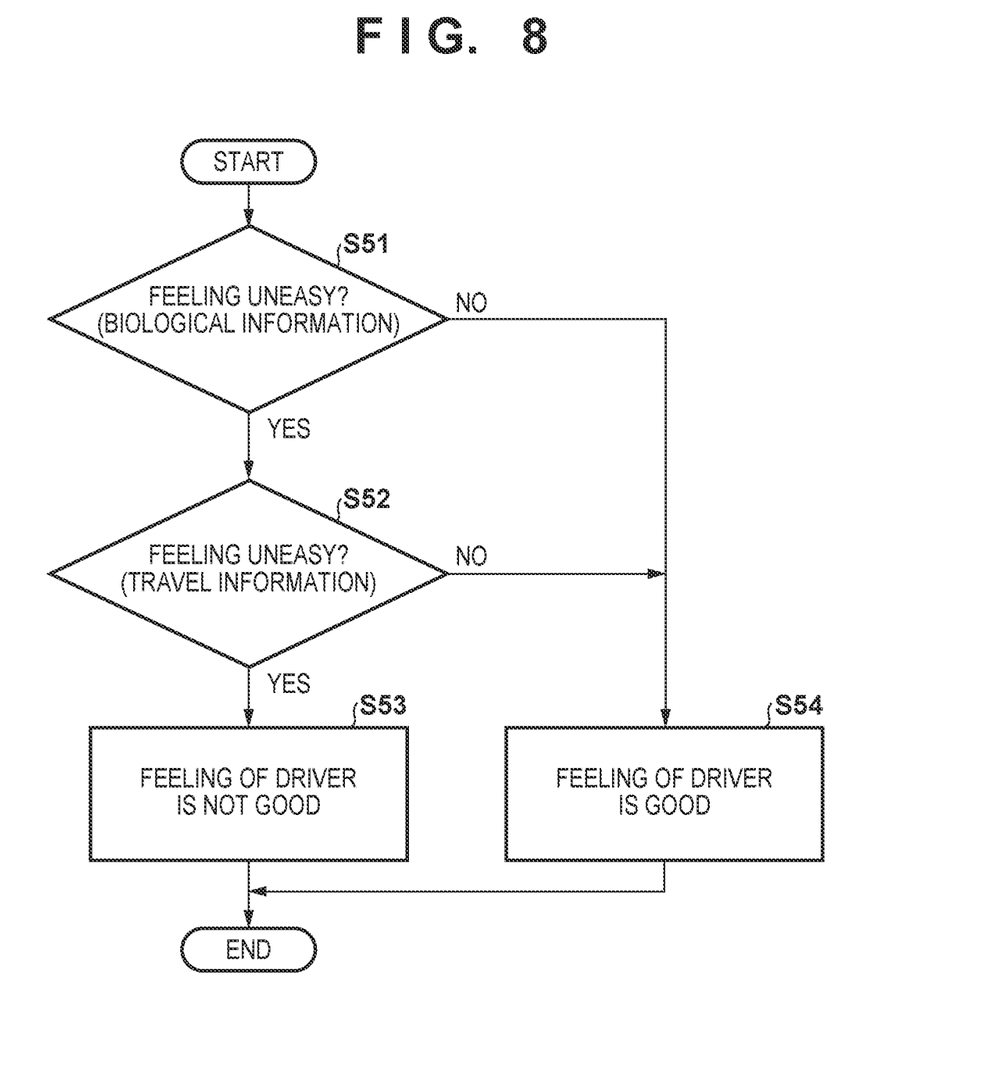
FIG. 8 is a flowchart showing an example of a method of estimating whether the feeling of a driver is good or not.

The method of estimating whether the feeling of the driver is good or not will be described below. FIG. 8 is a flowchart showing an example of the method of estimating whether the feeling of the driver is good or not. The steps of the flowchart shown in FIG. 8 can be performed by the estimation unit 21*a* of the server 20.

In step S51, based on the result of learning (deep-learning) data (big data) representing biological states (face images, heart rates, perspiration amounts, and respiration states) acquired for a number of drivers in the past, the estimation unit 21*a* judges, from biological information (the detection result of the biological detection unit) acquired from the vehicle 10, whether the driver is feeling uneasy. Upon judging that the driver is feeling uneasy, the process advances to step S52. On the other hand, upon judging that the driver is not feeling uneasy, the process advances to step S54, and it is estimated that the feeling of the driver is good.

In step S52, the estimation unit 21*a* judges, from traveling information (the detection result of the traveling detection unit) acquired from the vehicle 10, whether the driver is feeling uneasy. If the detection result of the traveling detection unit 11 does not smoothly change, and the driving is awkward, it is judged that the driver is feeling uneasy. The process advances to step S53, and it is estimated that the feeling of the driver is not good (bad). On the other hand, if the detection result of the traveling detection unit 11 smoothly changes, it is judged that the driver is not feeling uneasy. The process advances to step S54, and it is estimated that the feeling of the driver is good. Here, in the example shown in FIG. 8, the feeling of the driver is estimated as two types, that is, good or bad. However, the feeling of the driver may be estimated using a plurality of indices, for example, angry (irritated), impatient, sad, happy, and tense.

As described above, in this embodiment, the feeling of the driver is estimated, and a driving guidance according to the feeling of the driver is provided. Accordingly, it is possible to safely and appropriately improve the skill level of the driver in consideration of not only the skill level of the driver but also the feeling of the driver during the driving guidance.

Summary of Embodiment

1. An in-vehicle device according to the above embodiment is
an in-vehicle device that provides a driving guidance to a driver, comprising:
a determination unit (for example, 17*b*) for determining, for each of a plurality of items to provide a driving guidance, whether a difference between traveling information detected by a sensor of a vehicle (for example, 10) during traveling and ideal traveling information falls within an allowable range; and
a notification unit (for example, 17*c*) for notifying the driver of an item for which the determination unit determines that the difference does not fall within the allowable range in the plurality of items by performing highlighting on a display unit provided on the vehicle.

According to this embodiment, it is possible to provide a driving guidance such that the driving skill of the driver is efficiently improved.

2. In the above embodiment,
as highlighting of the item for which it is determined that the difference does not fall within the allowable range, the notification unit displays the item distinguishably from another item displayed on the display unit.

According to this embodiment, the driver can easily recognize for which item the difference does not fall within the allowable range.

3. In the above embodiment,
as highlighting of the item for which it is determined that the difference does not fall within the allowable range, the notification unit performs blinking.

According to this embodiment, the driver can easily recognize for which item the difference does not fall within the allowable range.

4. In the above embodiment,
the notification unit notifies, by a voice, the driver of the item for which it is determined that the difference does not fall within the allowable range.

According to this embodiment, the driver can aurally recognize for which item the difference does not fall within the allowable range.

5. In the above embodiment,
the in-vehicle device further comprises a selection unit for selecting the ideal traveling information from a plurality of pieces of ideal traveling information associated with a plurality of skill levels, respectively, in accordance with an estimation result of a feeling of the driver.

According to this embodiment, it is possible to safely and appropriately improve the skill level of the driver in consideration of the feeling of the driver during the driving guidance.

6. In the above embodiment,
the in-vehicle device further comprises a communication unit (for example, 16) for transmitting biological information of the driver detected by a sensor during traveling to a server (for example, 20) and receiving, from the server, the estimation result of the feeling of the driver obtained from the biological information.

According to this embodiment, it is possible to provide a driving guidance considering the feeling of the driver.

7. In the above embodiment,
the communication unit acquires a skill level of the driver from the server.

According to this embodiment, it is possible to provide a driving guidance according to the skill level of the driver.

8. In the above embodiment,
the selection unit selects ideal traveling information that should be used by the determination unit from the plurality of pieces of ideal traveling information based on the skill level of the driver and the estimation result of the feeling of the driver.

According to this embodiment, it is possible to provide a driving guidance while associating the feeling and the skill level of the driver with each other.

9. In the above embodiment,
the selection unit selects ideal traveling information corresponding to a skill level higher than the skill level of the driver if an estimation result representing that the feeling of the driver is good is obtained.

According to this embodiment, since the driving skill tends to improve in a case in which the feeling of the driver is good, it is possible to efficiently improve the driving skill of the driver.

10. In the above embodiment,
the selection unit selects ideal traveling information corresponding to a skill level equal to the skill level of the driver if an estimation result representing that the feeling of the driver is not good is obtained.

According to this embodiment, since the driving skill tends to be difficult to improve in a case in which the feeling of the driver is not good, it is possible to provide a driving guidance such that the driver can drive in a good feeling.

11. In the above embodiment,
the traveling information includes information concerning an operation of the vehicle, information concerning a posture of the driver, and information concerning a posture of the vehicle.

According to this embodiment, it is possible to provide a driving guidance from various viewpoints.

12. An information management server according to the above embodiment is
an information management server (for example, 20) communicably connected to an in-vehicle device, comprising:
a communication unit (for example, 23) for receiving traveling information of a vehicle detected by a sensor of the vehicle (for example, 10) and biological information of a driver from the in-vehicle device; and
an estimation unit (for example, 21a) for estimating a feeling of the driver based on the traveling information and the biological information.

According to this embodiment, it is possible to provide an appropriate driving guidance according to the feeling of the driver.

13. In the above embodiment,
the information management server further comprises an evaluation unit (for example, 21b) for evaluating a skill level of the driver based on the traveling information.

According to this embodiment, it is possible to know whether the skill level of the driver is improved, and also use the evaluated skill level for the next driving guidance and cumulatively improve the driving skill of the driver cumulatively.

14. An information management system according to the above embodiment is
an information management system (for example, 100) including an in-vehicle device that provides a driving guidance to a driver, and a server (for example, 20) communicably connected to the in-vehicle device, wherein
the in-vehicle device comprises:
a communication unit (for example, 16) for receiving an estimation result of a feeling of the driver from the server;
a determination unit (for example, 17b) for determining whether a difference between ideal traveling information selected in accordance with the estimation result of the feeling of the driver and traveling information detected by a sensor of a vehicle during traveling falls within an allowable range; and
a notification unit (for example, 17c) for notifying the driver of a determination result of the determination unit.

According to this embodiment, it is possible to provide an appropriate driving guidance according to the feeling of the driver.

15. A method according to the above embodiment is
a method of providing a driving guidance to a driver, characterized by comprising:
a determination step of determining, for each of a plurality of items to provide a driving guidance, whether a difference between traveling information detected by a sensor of a vehicle during traveling and ideal traveling information falls within an allowable range; and
a notification step of notifying the driver of an item for which it is determined in the determination step that the difference does not fall within the allowable range in the plurality of items by performing highlighting on a display unit provided on the vehicle.

According to this embodiment, it is possible to provide a driving guidance such that the driving skill of the driver is efficiently improved.

The present invention is not limited to the above embodiments, and various changes and modifications can be made within the spirit and scope of the present invention. Therefore, to apprise the public of the scope of the present invention, the following claims are made.

What is claimed is:

1. An in-vehicle device that provides a driving guidance to a driver, comprising:
a selection unit for selecting ideal traveling information from a plurality of pieces of ideal traveling information associated with a plurality of skill levels, respectively, in accordance with an estimation result of a feeling of the driver received from a server;
a determination unit for determining, for each of a plurality of items of both the ideal traveling information and an actual traveling information to provide a driving guidance, whether a difference between the actual traveling information detected by a sensor of a vehicle during traveling and the ideal traveling information selected by the selection unit falls within an allowable range; and
a notification unit for notifying the driver of an item for which the determination unit determines that the difference does not fall within the allowable range in the plurality of items.

2. The in-vehicle device according to claim 1, further comprising an acquisition unit for acquiring a plurality of pieces of ideal traveling information for a traveling route selected by the driver from a server in which a plurality of pieces of traveling route information each including a plurality of pieces of ideal traveling information are stored.

3. The in-vehicle device according to claim 1, wherein the selection unit switches the ideal traveling information to be selected in accordance with a change in the estimation result of the feeling of the driver during the driving guidance to the driver.

4. The in-vehicle device according to claim 1, further comprising a display unit for successively displaying the traveling information detected by the sensor of the vehicle during traveling and the ideal traveling information selected by the selection unit, in accordance with a position on the traveling route such that the difference can be recognized for each of the plurality of items.

5. The in-vehicle device according to claim 4, wherein the notification unit notifies the driver of the item for which the determination unit determines that the difference does not fall within the allowable range by causing the display unit to perform highlighting.

6. The in-vehicle device according to claim 5, wherein as highlighting of the item for which it is determined that the difference does not fall within the allowable range, the notification unit displays the item distinguishably from another item displayed on the display unit.

7. The in-vehicle device according to claim 5, wherein as highlighting of the item for which it is determined that the difference does not fall within the allowable range, the notification unit performs blinking.

8. The in-vehicle device according to claim 4, wherein
the plurality of items include positions of a plurality of parts of the driver during traveling, and
the notification unit notifies the driver of a part in the plurality of parts, for which it is determined that the difference does not fall within the allowable range, by performing highlighting of a corresponding portion of a driver model displayed by the display unit.

9. The in-vehicle device according to claim 1, wherein the notification unit notifies, by a voice, the driver of the item for which it is determined that the difference does not fall within the allowable range.

10. The in-vehicle device according to claim 1, further comprising a communication unit for transmitting biological information of the driver detected by a sensor during traveling to a server and receiving, from the server, the estimation result of the feeling of the driver obtained from the biological information.

11. The in-vehicle device according to claim 1, wherein the communication unit acquires a skill level information of the driver from the server.

12. The in-vehicle device according to claim 1, wherein the selection unit selects ideal traveling information that should be used by the determination unit from the plurality of pieces of ideal traveling information based on the skill level information of the driver and the estimation result of the feeling of the driver.

13. The in-vehicle device according to claim 12, wherein the selection unit selects ideal traveling information corresponding to a skill level higher than the skill level of the driver if an estimation result representing that the feeling of the driver is good is obtained.

14. The in-vehicle device according to claim 12, wherein the selection unit selects ideal traveling information corresponding to a skill level equal to the skill level of the driver if an estimation result representing that the feeling of the driver is not good is obtained.

15. The in-vehicle device according to claim 1, wherein the traveling information includes information concerning an operation of the vehicle, information concerning a posture of the driver, and information concerning a posture of the vehicle.

16. An information management system including an in-vehicle device that provides a driving guidance to a driver, and a server communicably connected to the in-vehicle device, wherein the in-vehicle device comprises:
a communication unit for receiving an estimation result of a feeling of the driver from the server;
a selection unit for selecting ideal traveling information from a plurality of pieces of ideal traveling information associated with a plurality of skill levels, respectively, in accordance with the estimation result received by the communication unit;
a determination unit for determining whether a difference between ideal traveling information selected by the selection unit and an actual traveling information detected by a sensor of a vehicle during traveling falls within an allowable range, wherein the ideal traveling information and the actual traveling information comprise a plurality of items; and
a notification unit for notifying the driver of a determination result of the determination unit.

17. A method of providing a driving guidance to a driver, comprising:
a selection step of selecting ideal traveling information from a plurality of pieces of ideal traveling information associated with a plurality of skill levels, respectively, in accordance with an estimation result of a feeling of the driver received from a server;
a determination step of determining, for each of a plurality of items to provide a driving guidance, whether a difference between an actual traveling information detected by a sensor of a vehicle during traveling and the ideal traveling information selected in the selection step falls within an allowable range, wherein the ideal traveling information and the actual traveling information comprise a plurality of items; and
a notification step of notifying the driver of an item for which it is determined in the determination step that the difference does not fall within the allowable range in the plurality of items.

* * * * *